United States Patent [19]

Arntz et al.

[11] Patent Number: 5,015,789
[45] Date of Patent: May 14, 1991

[54] METHOD OF PREPARING 1,3-PROPANEDIOL

[75] Inventors: Dietrich Arntz, Oberursel; Norbert Wiegand, Hanau, both of Fed. Rep. of Germany

[73] Assignee: Degussa Aktiengesellschaft, Frankfurt, Fed. Rep. of Germany

[21] Appl. No.: 563,152

[22] Filed: Aug. 3, 1990

[30] Foreign Application Priority Data

Aug. 8, 1989 [DE] Fed. Rep. of Germany ....... 3926136

[51] Int. Cl.$^5$ ...................... C07C 29/14; C07C 31/20; C07C 47/19; C07C 45/64
[52] U.S. Cl. ..................................... 568/862; 568/458
[58] Field of Search ................................ 568/862, 458

[56] References Cited

U.S. PATENT DOCUMENTS 2,421,451  6/1947  Balcar .................................. 568/862
2,434,110  1/1948  Hatch et al. ........................ 568/458
2,638,479  5/1953  Ballard et al. ...................... 260/468
3,518,310  6/1970  Lutz .................................... 568/862
3,536,763  10/1970  Eleuterio et al. ................... 568/862

FOREIGN PATENT DOCUMENTS 2054601  5/1972  Fed. Rep. of Germany ...... 568/862

Primary Examiner—J. E. Evans
Attorney, Agent, or Firm—Beveridge, DeGrandi & Weilacher

[57] ABSTRACT

A method for preparing 1,3-propanediol is disclosed which comprises the hydration of acrolein in the presence of an acidic cation exchanger resin and the hydrogenation of the 3-hydroxypropionaldehyde obtained in the first stage. The volume-time yield was able to be increased in the hydration stage by using a cation exchanger resin with phosphonic acid groups, preferably a cation exchanger with chelating aminophosphonic acid groups. The hydrogenation catalyst can be repeatedly reused without appreciable loss of activity.

12 Claims, No Drawings

METHOD OF PREPARING 1,3-PROPANEDIOL

INTRODUCTION AND BACKGROUND

The present invention relates to a method of preparing 1,3-propanediol by means of the hydration of acrolein in the presence of an acidic cation exchanger followed by the subsequent catalytic hydrogenation of the 3-hydroxypropionaldehyde.

1,3-propanediol has many potential applications as a monomeric component for the production of polyesters and polyurethanes as well as an initial starting material for the synthesis of cyclic compounds. Many methods have already been suggested for the preparation of 1,3-propanediol, including those which involve a molecular synthesis from a $C_2$ component and a $C_1$ component and those which start from a $C_3$ component such as acrolein in particular.

As is known from U.S. Pat. No. 2,434,110, acrolein can be hydrated in the presence of an acidic catalyst to form 3-hydroxypropionaldehyde. The reaction preferably takes place at an elevated temperature using a 5 to 30% by weight solution of acrolein in water and an acid such as for example sulfuric acid, phosphoric acid or acidic salts of these acids as the catalyst. The reaction mixture obtained during the hydration is hydrogenated, optionally after removal of nonreacted acrolein, in the presence of customary hydrogenation catalysts. Catalysts containing one or more metals active in hydrogenation reactions such as for example Fe, Co, Ni, Cu, Ag, Mo, W, V, Cr, Rh, Pd, Os, Ir and Pt are suitable as catalysts for the hydrogenation of 3-hydroxypropionaldehyde to 1,3-propanediol.

A disadvantage in the method of U.S. Pat. No. 2,434,110 are the low yields of 1,3-propanediol, which are attributable especially to acrolein—consuming condensation reactions during the hydration stage. In addition, the selectivity of the mineral acid catalyzed hydration reaction is dependent to a very large extent on the conversion of acrolein. In order to achieve an acceptable selectivity, the hydration reaction is terminated at a low acrolein conversion, which, however, results in a poor volume-time yield.

There has been no shortage of attempts to obviate the disadvantages of the above described method, for example by means of the addition of lower carboxylic acids onto the double bond of the acrolein. However, this makes a saponification step necessary after the hydrogenation. In addition, the recycling of the carboxylic acid poses problems (U.S. Pat. No. 2,638,279). The hydration of acrolein using carbon dioxide as the catalyst is also known however, this method requires long reaction times—cf. DE-OS 19 05 823.

It has been determined that although the hydration of acrolein can be carried out using for example phosphoric acid or dihydrogen phosphates catalyst but problems occur in the subsequent hydrogenation of the reaction mixture freed from non-reacted acrolein.

When very active nickel hydrogenation catalysts are used, both the hydrogenation conversion and also the reaction speed drop rapidly upon repeated use of the catalyst. This leads to an elevated consumption of catalyst.

In addition, the presence of the hydration catalyst during working up by distillation results in product losses due to decomposition or, in the case of first carrying out a neutralization, results in cloggings and encrustations in the system. The problems indicated above can be partly obviated if the hydration catalyst is removed from the reaction mixture before hydrogenation by means of ion exchange resins or by separating 3-hydroxypropionaldehyde from the reaction mixture and then subjecting it to hydrogenation. However, both alternative measures for reducing the consumption of expensive hydrogenation catalyst necessitate additional equipment, lead to a higher consumption of energy and, additionally, in wastewater problems, thus increasing the production costs for 1,3-propanediol.

According to the method of U.S. Pat. No. 3,536,763, the hydration step is carried out in the presence of weakly acidic cation exchanger resins the functional groups of which are carboxyl groups at 40° to 120° C. Preferably, 0.1 to 5% of the functional groups should be present in the form of an alkali carboxylate, alkaline earth carboxylate or earth metal carboxylate. The yields of 3-hydroxypropionaldehyde are indicated to be approximately 80%, and are said to be substantially independent of the acrolein conversion in the range of 25 to 65%. This process also comprises the known hydrogenation of 3-hydroxypropionaldehyde to 1,3-propanediol.

Although the catalytic activity of the ion exchanger resins with carboxyl groups was confirmed when the method of U.S. Pat. No. 3,536,763 was followed, the level of effectiveness suggested that these ion exchangers would not be suitable for use in industrial systems. It turned out that these catalysts require rather high temperatures and rather long reaction times, which runs counter to the desired high volume-time yield.

SUMMARY OF THE INVENTION

An object of the present invention is to provide an improved method of preparing 1,3-propanediol by means of the hydration of acrolein in the presence of acidic cation exchanger resins with subsequent catalytic hydrogenation which can be carried out with a rather high volume-time yield and good selectivity in the hydration stage. Also, the reaction mixture obtained during the hydration should not impair the activity of the hydrogenation catalyst in order to make it possible to reuse the catalyst in following batches, thereby enabling the economy of the method to be improved.

The method of the invention for preparing 1,3-propanediol is carried out by means of hydrating acrolein in the presence of an acidic cation exchanger resin with the formation of 3-hydroxypropionaldehyde. Acrolein and water are reacted in a weight ratio of 1:2 to 1:20 at 30° to 120° C. and a pressure in a range from 1 to 20 bars. Separation of the ion exchanger resin and, to the extent it is present, of the nonreacted acrolein from the reaction mixture is carried out by known methods. The 3-hydroxypropionaldehyde formed thereby is then catalytically hydrogenated under known conditions in the liquid or gaseous phase using customary hydrogenation catalysts.

A feature of the invention resides in using cation exchanger resins with phosphonic acid groups.

The cation exchanger resins to be used in accordance with the invention contain acidic phosphonic acid groups. The phosphonic acid groups can also be present in part as acidic salts of alkali metals or alkaline-earth metals, but in general the free phosphonic acid groups are preferred.

The ion exchangers, which are insoluble in the reaction medium, are based on a polymer matrix with crosslinkages and contain the phosphonic acid groups responsible for the catalytic activity in chemically incorporated form. The phosphonic acid group is preferably bonded to an aliphatic carbon atom. Ion exchangers with chelating aminophosphonic acid groups in which an amino group is connected by one or two carbon atoms to the phosphonic acid group are especially suitable. Exchanger resins with a polystyrene matrix which are cross-linked with divinyl benzene and which contain aminomethane phosphonic acid groups with the structure $-NH-CH_2-PO_3H_2$ as functional groups exhibit excellent properties when used in the method of the invention. The density of the functional groups is in general in the range of 1 to 3 equivalents ($H^+$ form) per 1 exchanger resin. The exchanger resin is preferably used in the bead form typical for ion exchangers.

Acrolein and water are supplied to the hydration stage in a weight ratio of 1:2 to 1:20, preferably 1:3 to 1:10, and most preferably 1:3 to 1:6. The reaction to form 3-hydroxypropionaldehyde takes place in a temperature range from 30° to 120° C. A temperature in the range of 40° C. to above 100° C. is preferred. A temperature below 40° C. generally results in long reaction times, while a temperature above 100° C. leads to a reduced selectivity and to problems concerning the useful life of the exchanger resins. In a particularly preferred embodiment, the hydration takes place at 50° to 90° C.

In temperatures below the boiling point of acrolein, the reaction can take place at normal pressure or under moderate pressure. At reaction temperatures around or above the boiling point of acrolein, the reaction is carried out under a pressure in a range of approximately 2 to 20 bars. In a particularly preferred temperature range of 50° to 90° C., a pressure in a range of 2 to 5 bars has proven to be suitable.

Usually, the selectivity of the reaction of water with acrolein to form 3-hydroxypropionaldehyde decreases with an increasing conversion of acrolein. A comparable decrease of selectivity was also observed in the case of the cation exchangers with carboxyl groups. A lowering of the acrolein conversion from approximately 80% to approximately 30% increases the yield of 1,3-propanediol, approximately 60% to over 80% based on the acrolein conversion, if the mixture from the hydration step is hydrogenated with Raney nickel, after distilling off the unreacted acrolein. An acrolein conversion between 30 and 80%, particularly 40 to 60%, is therefore preferred.

If desired, polymerization inhibitors such as for example hydroquinone, hydroquinone monomethyl ether or butylated phenols can be added in an effective amount to the acrolein-water mixture.

The hydration can be carried out discontinuously and continuously and known reactors such as for example, agitated or stirred reactors, loop type reactors, fluidized bed reactors, floating bed reactors and flow tube reactors can be used. Reactors operating in accordance with the flow tube principle are preferred over loop reactors and stirred reactors. The through flow rate in a flow tube containing the acidic cation exchanger with the phosphonic acid groups and provided with a heatable jacket as well as the reaction temperature are adjusted so that the desired acrolein conversion is achieved. The reaction mixture can also be passed through the ion exchanger bed provided that large dead volumes are avoided in which the reaction mixture is present at reaction temperature in the absence of the hydration catalyst.

After separation of the ion exchanger, which usually takes place by means of sedimentation or filtration or is essentially automatic where known devices for the ion exchange, are used, the reaction mixture is freed from unreacted acrolein as far as necessary. This measure is always recommended for an acrolein conversion between 30 to 80% because acrolein, even if it was separated as aqueous acrolein, can be returned directly into the process. The separation of the acrolein can be carried out in a known manner, especially by distillation, preferably under reduced pressure and at temperatures below 80° C. It is especially advantageous to deliver the reaction mixture to a thin-layer evaporator, in which both unreacted acrolein and as well as a part of the water of the reaction mixture are distilled off together under moderate conditions. In this way, a concentrated, aqueous solution of 3-hydroxypropionaldehyde is obtained as the sump product, which has an advantageous effect on the hydrogenation step and the energy consumption of the process.

If desirable, the 3-hydroxypropionaldehyde can be extracted from the aqueous reaction mixture freed from the acrolein by means of polar organic solvents, such as for example a lower ester or isobutanol, and can be supplied in this form to the hydrogenation step. Although this embodiment leads to a rapid uptake of hydrogen in the hydrogenation stage, this advantage is offset by the considerable technical complexity involved in the extraction and recovery of the organic solvent. Accordingly, the direct hydrogenation of the aqueous 3-hydroxypropionaldehyde is preferred.

The catalytic hydrogenation of the 3-hydroxypropionaldehyde in the liquid phase is carried out in a known manner and in typical hydrogenation reactors. The catalyst can be present either in suspended form per se or in supported form or can be a component of fixed-bed catalysts. Homogeneous catalysts can also be used. Particularly suitable suspension catalysts are Raney nickel, which can be doped with various other catalytically active metals, as well as platinum on activated carbon. Among the fixed-bed catalysts, the substances mentioned in U.S. Pat. No. 2,424,110 can be used. Nickel catalysts have proven to be especially effective catalysts. A high volume-time yield is achieved in the hydrogenation stage if the solution to be hydrogenated has a pH in a range of 2.5 to 6.5, preferably about 6 and the hydrogenation temperature is in a range from 25° to 100° C.

In principle, 3-hydroxypropionaldehyde can also be catalytically hydrogenated in the gaseous phase, shown in DE-PS 20 54 601, so that this embodiment of hydrogenation can also follow the hydration of the invention.

As follows from the examples set forth below the cation exchangers with phosphonic acid groups to be used in accordance with the invention enable a considerably higher volume-time yield to be achieved than was the case with the previously known ion exchangers with carboxyl groups. The advantageous effect of the ion exchanger resins containing phosphonic acid groups is a consequence of the higher reactivity. At the same time, the reaction temperature can be kept lower, thereby achieving a higher selectivity. Whereas LHSV (liquid hourly space velocity) values around 0.6 hours$^{-1}$ were obtained in tests carried out under comparable conditions in the same apparatus using the exchanger resins of the invention, the LHSV values in the case of the ion exchangers according to U.S. Pat. No. 3,536,763 were only around 0.4 hours$^{-1}$.

In the hydrogenation of aqueous 3-hydroxypropanaldehyde solutions prepared in accordance with the invention, nickel hydrogenation catalysts are deactivated much more slowly than in the case of solutions still containing phosphate emanating from the hydration step. Accordingly, the catalyst can be repeatedly reused in the method of the invention.

DETAILED EMBODIMENTS OF THE INVENTION

EXAMPLES 1 and 2

Hydration of acrolein using a weakly acidic ion exchanger (Lewatit CNP 80 of Bayer AG)—example 1/state of the art—and using an acidic ion exchanger with aminophosphonate groups (Duolite C 467 of Rohm & Haas)—example 2/in accordance with the invention—in a recirculation apparatus at 40° C.

The recirculation apparatus comprises a double-jacket glass column (length 600mm, inner diameter 25 mm) which is charged with 300 ml ion exchanger resin, a recirculation pump in the recirculation line, a 2-liter storage vessel, specimen removal connections, a pH electrode and a thermometer and also a reflux condenser for pressure equalization.

The ion exchanger is converted in a known manner into the H form. Subsequently, the entire apparatus is flushed with 1 liter of the aqueous acrolein solution. After recharging of the apparatus with 950 m aqueous acrolein solution, (17.8% by weight) this solution is pumped through the ion exchanger resin (2.7 l/h) several hours at 40° C. and the progress of the hydration reaction is followed by gas chromatography—acrolein and 3-hydroxypropionaldehyde (HPA)—and by aldehyde titration.

The results obtained are shown in the following table:

changer with the aminophosphate groups of the invention. Moreover, the trend of the aldehyde concentration as determined by titration suggests a secondary product formation in the case of the ion exchangers to be used in accordance with the invention.

EXAMPLES 3 to 7

In a pilot scale apparatus comprising a loop-type reactor, known cation exchanger resins continuing carboxyl groups (examples 3,4) and cation exchanger resins of the invention containing aminophosphonate groups (examples 5 to 7) were compared with each other in continuous operation at different temperatures and different residence times in order to determine the volume-time yield; expressed here as LHSV value.

The apparatus consists essentially of units for preparing and introducing the aqueous acrolein solution, the reaction loop, receivers for receiving the reaction product as well as safety devices, measuring devices and control devices. The reaction loop (6.2 liters) consists of a double-jacketed tube for thermostatically controlling reaction solution, a recirculation pump and the actual reaction tube, which contains the catalytic bed; i.e. 4 liters ion exchanger resin. An outlet pipe runs from the reaction loop via a filter and control valve to the receivers.

The ion exchanger resins are converted in a known manner into the H form and washed free of acid. After the reaction tube has been filled with the ion exchanger and after an operational test of the system, acrolein and water were introduced in the desired ratio into the reaction loop and circulated (approximately 190 l/h).

After establishment of the acrolein 3-hydroxypropionaldehyde equilibrium, which is confirmed by a gas-chromatographic analysis of specimens, the actual continuous operation begins, during which temperature, pressure, volume flows and composition are detected and determined. The following table shows the

| | | | | CHO conc. titr. % of input | Concentration | | Ac Conversion % | Selectivity % |
|---|---|---|---|---|---|---|---|---|
| Example No. | Ion exchanger | Time h | pH | | Ac. % by weight | HPA % by weight | | |
| 1 | Lewatit CNP 80 | 0 | | 100 | 17.7 | — | — | — |
| | | 1 | 3.6 | 95.4 | 17.0 | — | 4.0 | — |
| | | 3 | 3.7 | 91.0 | 16.0 | 0.2 | 9.2 | 11 |
| | | 6 | 3.9 | 85.8 | 14.4 | 0.8 | 18.2 | 18 |
| 2 | Duolite C 467 | 0 | | 100 | 18.2 | — | — | — |
| | | 1 | 3.8 | 95.7 | 16.2 | 1.6 | 10.9 | 62 |
| | | 3 | 3.8 | 94.0 | 14.6 | 3.2 | 19.3 | 69 |
| | | 6 | 3.9 | 90.9 | 12.9 | 5.2 | 28.9 | 75 |
| | | 7 | 3.9 | 90.9 | 12.4 | 5.8 | 31.8 | 76 |

Ac = acrolein
HPA = 3-hydroxypropionaldehyde
CHO-conc. titr. = aldehyde concentration as determined by oxime titration
Ac and HPA were quantitively determined by gas chromatopgraphy with multipoint calibration via an internal standard using a Porapak P column.

As can be seen from the trend of the acrolein and HPA concentration, the ion exchanger with carboxyl groups is considerably less active than the ion exchanger with carboxyl groups is considerably less active than the ion exchanger essential operating parameters and the results of analysis.

| Example No. | Exchanger Resin | Acrolein conc. % by weight | Ac/H$_2$O input l/h | Reaction temp. °C. | Average residence time h | LHSV h$^{-1}$ | Acrolein Conversion % | HPA yield based on Ac conversion % |
|---|---|---|---|---|---|---|---|---|
| 3 | Lewatit CNP 80 | 19.3 | 1.09 | 80 | 5.69 | 1.27 | 65.0 | 61.0 |
| 4 | Lewatit CNP 80 | 21.7 | 1.61 | 80 | 3.84 | 0.40 | 53.9 | 67.0 |
| 5 | Duolite | 19.8 | 1.55 | 80 | 3.99 | 0.39 | 70.7 | 65.1 |

-continued

| Example No. | Exchanger Resin | Acrolein conc. % by weight | Ac/H$_2$O input 1/h | Reaction temp. °C. | Average residence time h | LHSV h$^{-1}$ | Acrolein Conversion % | HPA yield based on Ac conversion % |
|---|---|---|---|---|---|---|---|---|
| 6 | Duolite C 467 | 20.2 | 2.46 | 80 | 2.51 | 0.62 | 63.7 | 71.0 |
| 7 | Duolite C 467 | 20.3 | 2.45 | 60 | 2.52 | 0.61 | 40.8 | 82.0 |

A comparison of example 4 (state of the art) with 5 (in accordance with the invention) shows that under comparable operating conditions using the ion exchanger of the invention, the conversion can be increased without loss of selectivity by approximately 15% over that of the state of the art. In addition, it is possible—cf. example 6—when using the ion exchanger of the invention to raise the LHSV value by approximately 50%, the conversion being only moderately lower but at the same time the selectivity rises: the volume-time yield that is, the amount of hydroxypropionaldehyde produced per unit of time and reactor volume, is increased in this manner by over 50 % (in comparison to example 4). As can be given from a comparison of example 7 with example 4, a considerably higher volume-time yield can still be obtained in accordance with the invention at a reaction temperature which is 20° C. lower than was possible according to the state of the art.

EXAMPLE 8

Hydrogenation of an aqueous solution of 3-hydroxypropionaldehyde (HPA) obtained according to example 6 on a fixed-bed catalyst (Ni/Al$_2$O$_3$/SiO$_2$).

Using a thin-film evaporator, the reaction solution of example 6 is freed from unreacted acrolein and, at the same time, from a part of the water at approximately 65° C. and under reduced pressure. 750 ml of an aqueous solution containing 1.49 moles HPA are introduced into the hydrogenation reactor of standard design and are circulated over 140 g catalyst. The mixture is hydrogenated for 4 hours at approximately 55° C. at a hydrogen pressure of 150 bars which drops during the hydrogenation to 106 bars. The HPA conversion is 100% and the yield of 1,3-propanediol is 78% (quantitative gas chromatography). The reaction solution is worked up in a known manner by distillation.

EXAMPLES 9 to 11

A mixture of acrolein and water is reacted in a continuous laboratory apparatus with a flow-tube reactor containing the cation exchanger resin of the invention with aminophosphonate groups. The HPA solution which is produced catalytically is hydrogenated after separation of the unreacted acrolein and the 1,3-propanediol obtained is determined.

The apparatus consists essentially of equipment for preparing and introducing the aqueous acrolein solution, the reactor consisting of three 2500 mm long thermostatically controlled stainless steel tubes connected in series and filled with a total of 11.6 liters ion exchanger resin, and of filters, receivers and measuring and control instruments.

Hydrogenation of 3-hydroxypropionaldehyde (HPA) using a Raney nickel type catalyst An 18.3% by weight acrolein solution is pumped for 6 hours through two of the three tubes filled with ion exchanger resin at a reactor temperature of 50° C. with a catalyst load of LHSV=0.25 h$^{-1}$. The acrolein conversion is 49.0%. The solution obtained is freed from acrolein in a gentle vacuum in a known manner and hydrogenated in portions in a high-pressure autoclave using 11.6 g of a nickel-containing suspension catalyst per kg solution at 50° C. and an initial hydrogen pressure of 135 bars with repeated use of the catalyst. After filtering, the entire solution is freed from most of the water in a rotary evaporator and the 1,3-propanediol is recovered from the residue by vacuum distillation in a 77.0% yield based on the acrolein reacted.

Hydrogenation of 3-hydroxypropionaldehyde (HPA) using a noble-metal catalyst

An HPA solution which was obtained as in the preceding example by pumping an 18.6% by weight acrolein solution through the described three reactor tubes at 58° C. with a catalyst load of LHSV=0.22 h$^{-1}$ and an acrolein conversion of 69.1% and then freed from unreacted acrolein is hydrogenated in the same manner as was described in example 9, except that the nickel-containing hydrogenation catalyst is replaced by a powdery platinum/activated-carbon catalyst with a platinum content of 10%. The 1,3-propanediol obtained is determined by means of gas chromatography in the solution concentrated by evaporation. The selectivity is 74.5% based on reacted acrolein.

An HPA solution obtained in basically the same manner by pumping a 17.5% by weight acrolein solution through one of the reactor tubes filled with ion exchanger resin of the invention at 58° C., a catalyst load of LHSV=0.69 h$^{-1}$ and an acrolein conversion of 34.9% is hydrogenated as in the preceding example after separation of the unreacted acrolein. The selectivity, determined by quantitative gas chromatography, is 85.1% relative to reacted acrolein.

Further variations and modifications of the foregoing will be apparent to those skilled in the art and are intended to be encompassed by the claims appended hereto.

German priority application P 39 26 136.0 is relied on and incorporated by reference.

We claim:

1. A method of preparing 1,3-propanediol comprising hydrating acrolein in the presence of an acidic cation exchanger resin to form 3-hydroxypropionaldehyde, by reacting acrolein and water in a weight ratio of 1:2 to 1:20 at 30° to 120° C. and a pressure in a range from 1 to 20 bars in the presence of a cation exchanger resin having phosphonic acid groups, or salts thereof, separating said ion exchanger from the resulting reaction mixture and, to the extent it is present, unreacted acrolein to obtain 3-hydroxypropionaldehyde and subsequently catalytically hydrogenating the 3-hydroxypropionaldehyde in the liquid or gaseous phase using a hydrogenation catalyst therefor.

2. The method according to claim 1, wherein the cation exchangers resin has chelating aminophosphonic acid groups.

3. The method according to claim 1, wherein acrolein and water are used in the weight ratio of 1:3 to 1:6.

4. The method according to claim 1, wherein the hydrating is carried out at 50° to 90° C.

5. The method according to claim 1, further comprising hydrating until an acrolein conversion of 30 to 80% is reached, separating the ion exchanger resin and then distilling unreacted acrolein from the aqueous reaction mixture for return into the hydration stage.

6. The method according to claim 1, further comprising hydrating in a flow tube and obtaining the desired acrolein conversion by passing the reaction mixture once through the flow tube.

7. The method according to claim 1 wherein the catalytic hydrogenation of the 3-hydroxypropionaldehyde is carried out in aqueous solution at a pH in a range of 2.5 to 6.5 and at a temperature of 50° to 90° C.

8. The method according to claim 1, wherein the catalytic hydrogenation of the 3-hydroxypropionaldehyde is carried out in the presence of nickel-containing suspension catalyst or fixed-bed catalyst.

9. The method according to claim 1, wherein the cation exchanger resin contains phosphonic acid salts of an alkali metal or alkaline earth metal.

10. The method according to claim 1, wherein the exchanger resin has a polystyrene matrix cross-linked with divinyl benzene and which contains aminomethane phosphonic acid groups with the structure —NH—CH$_2$—PO$_3$H$_2$.

11. The method according to claim 1, wherein the phosphonic functional groups is present in the range of 1 to 3 equivalents (H$^+$ form) per 1 exchanger resin.

12. The method according to claim 1 where a polymerization inhibitor is added to the acrolein-water mixture.

* * * * *